Figure 1:
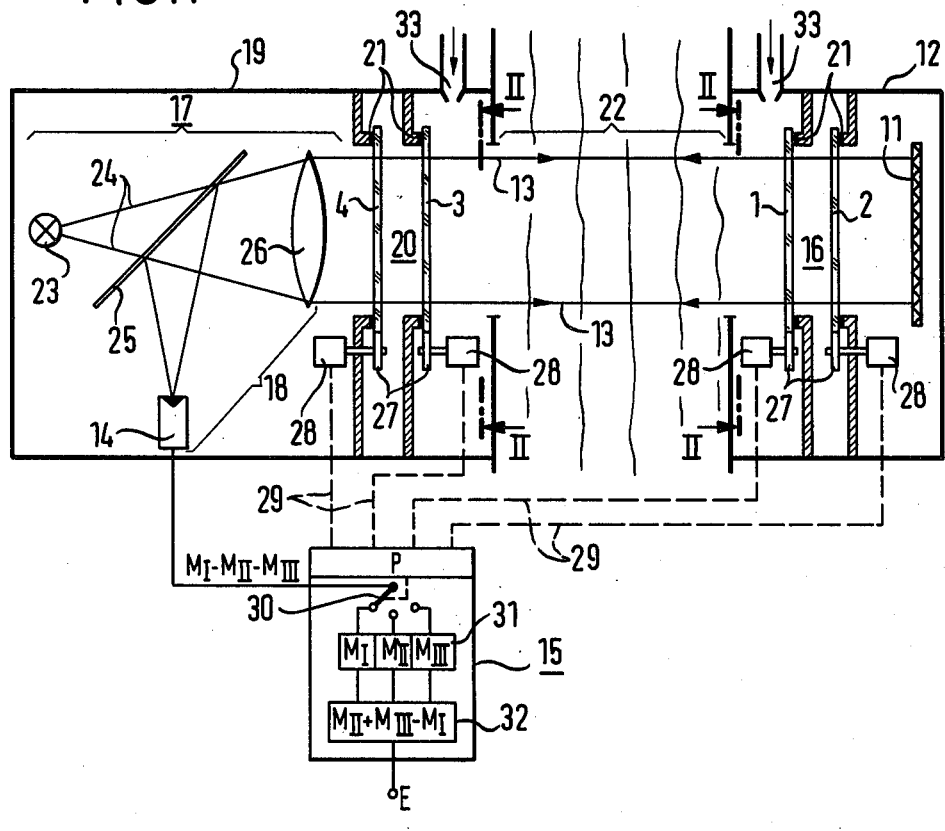

United States Patent [19]

Krause

[11] 4,432,649

[45] Feb. 21, 1984

[54] OPTICAL APPARATUS FOR MEASURING TRANSMISSION OR ABSORPTION ALONG A MEASUREMENT PATH

[75] Inventor: Gerhard Krause, Wachtelweg 26e, 8200 Rosenheim-Egarten, Fed. Rep. of Germany

[73] Assignee: Gerhard Krause, Waldkirch, Fed. Rep. of Germany

[21] Appl. No.: 270,469

[22] Filed: Jun. 4, 1981

[30] Foreign Application Priority Data

Jun. 12, 1980 [DE] Fed. Rep. of Germany ....... 3022114

[51] Int. Cl.³ .......................................... G01N 21/59
[52] U.S. Cl. ..................................... 356/438; 250/573
[58] Field of Search ............... 356/437, 438, 439, 440; 250/573, 575, 570

[56] References Cited

U.S. PATENT DOCUMENTS

| | | | |
|---|---|---|---|
| 3,251,999 | 5/1966 | Middleton et al. | 356/439 |
| 3,838,925 | 10/1974 | Marks | 356/438 |
| 3,885,162 | 5/1975 | Geertz | 356/439 |
| 3,949,234 | 4/1976 | Vandermark | 356/439 |
| 4,247,205 | 1/1981 | Typpo | 356/440 |

Primary Examiner—R. A. Rosenberger
Attorney, Agent, or Firm—Townsend and Townsend

[57] ABSTRACT

A light transmitter transmits a beam of light along a measurement path to a light receiver which receives the light beam either directly or via a retro-reflector. The light receiver forms electrical signals representative of the transmission or absorption along the measurement path. In an arrangement with separate light transmitter and receiver units these units are arranged in respective housings at each end of the measurement path. In an alternative arrangement in which the light transmitter and receiver are in a single unit a retro-reflector is positioned at the other end of the measurement path. In this alternative arrangement the light transmitter/receiver unit is embodied in one housing and the retro-reflector in a second housing. In either arrangement both housings are sealingly closed by at least one and preferably two windows which can be moved cyclically into and out of the light beam. The transmission or absorption along the measurement path is calculated from the signals in such a way that the measured absorption is independent of the prevailing level of contamination. The apparatus is particularly useful for transmission measurements in chimneys and on airfields.

27 Claims, 2 Drawing Figures

OPTICAL APPARATUS FOR MEASURING TRANSMISSION OR ABSORPTION ALONG A MEASUREMENT PATH

The invention relates to optical apparatus for measuring transmission or absorption along a measurement path and has particular reference to apparatus of the type comprising a light transmitter for transmitting a light beam along the measurement path, a light receiver for receiving said light beam from said light transmitter after it has passed along said measurement path, either directly or via a light deflector with the light receiver forming electrical signals representative of the transmission or absorption along the measurement path.

Many variants of this type of apparatus are known. They are used, by way of example, for smoke density measurements or to determine the concentrations of components of an exhaust gas mixture through which the measurement path passes (German Auslegeschrift No. 21 30 331 and German Auslegeschrift No. 25 21 934). All these types of measuring apparatus are subject to a common problem, namely that both the light transmitter and receiver and, if provided, the light deflector are located adjacent a measurement path in a very aggressive environment which can seriously impair the operation of the measuring apparatus. Measuring apparatus of this kind is for example arranged on smoke stacks in order to determine the concentrations of specific components in the flue gas. The disadvantageous environmental conditions to which measuring apparatus of this kind is subjected include, by way of example, a high air humidity (up to 95% relative humidity), an aggressive atmosphere ($HCl$, $H_2SO_3$ etc.), environmental temperatures from $-30$ C. to $+60$ C., vibrational loads up to 3 g and dust and aerosol charges in the atmosphere of the measuring path which can reach several hundred gramms per cubic meter of gas. Difficulties arise not only when using measuring apparatus of this kind in the exhaust flues of combustion plant but also in foggy contaminated environments such as prevail at airports, roads or tunnels where atmospheric contamination or fog density is to be measured.

The optical surfaces of the measuring apparatus which are exposed to the contamination charged measuring path become contaminated or dirtied more or less quickly depending on the operating conditions (pressure below atmospheric pressure pressure above atmospheric pressure, periodic operation, full-time operation etc.). The contamination of the optical boundary surfaces leads to a falsification of the measurement result.

The usual requirement for a transmissometer is that, in the most sensitive measurement range with an extinction $E=0.09$, $\tau=18\%$, it should achieve a measurement accuracy of 2% (in absorption), i.e. it must then be possible to determine changes in transmission of 0.04% without difficulty. In this case even trivial contamination of the transparent optical boundary surfaces of the light reflector can seriously impair the measurement accuracy.

The measurement techniques for taking contamination into account have hitherto been restricted to the light transmitter/receiver side of auto-collimation measurement apparatus. In this connnection a so-called zero-point reflector which can be periodically swung into the light beam has, for example, been arranged in the optical head as the last optical element before the measurement path. The light beam periodically reflected from the zero-point reflector is then used for calibration purposes. This assumes that the zero-point reflector is not subject to contamination. In practice the progress of the contamination can be delayed by technical measures such as the arrangement of the zero-point reflector in a protective pocket but cannot however be completely removed. The use of the known zero-point reflector results effectively in the realization of a reference channel of a modified two beam photometer which includes the contamination of the optical boundary surfaces (apart from the zero-point reflector itself). If the contamination amounts for example to 6% of the deflection in any one case then a boundary value is reached at which an alarm is initiated to indicate that cleaning of the optical surfaces is required. Up to now it has not proved possible to assess the contamination at the reflector side of the apparatus.

The principle object underlying the present invention is thus to provide optical measurement apparatus of the initially named kind in which the measurement and the processing of signal changes brought about by contamination are carried out by the measuring apparatus itself with the signal changes being utilized in a simple manner to provide a measurement signal which is unaffected by contamination.

In order to accomplish this object there is provided, in accordance with the invention, optical apparatus for measuring transmission or absorption along a measurement path, the apparatus comprising a light transmitter for transmitting a light beam along the measurement path, a light receiver for receiving said light beam from said light transmitter after it has passed along said measurement path, either directly or via a light deflector, with said light receiver forming signals representative of the transmission or absorption along the measurement path and wherein at least one of said light transmitter, said light receiver and said light deflector is accommodated in a housing which is sealingly closed by at least one window which can be removed cyclically into and out of said light beam.

In one preferred embodiment the light receiver is positioned to receive light directly from the light transmitter and both the light transmitter and light receiver are arranged in respective housings each of which is provided with a said at least one window.

In a further preferred embodiment the light receiver and the light transmitter are arranged in a common housing at one end of the measuring path a light deflector, which is conveniently a retro-reflector, is arranged in a further housing at the other end of the measuring path and both the common housing and the further housing are provided with a said at least one window.

In either of the above arrangements each said housing is usefully provided with a respective second window which can be moved out of the light beam. Each said second window can be replaced by an equivalent window which is normally shielded from external influences.

The arrangement is usefully such that each of said second windows is arranged closely behind the associated first said window thereby providing a narrow chamber therebetween with each second window acting to sealingly separate the associated narrow chamber from the interior of the associated housing. When using an arrangement with a light deflector in the form of a reflector, a further reflector which is normally protected from contamination can be substituted for the actual reflector during the contamination measurement. In this arrangement the further reflector can be thought of as taking the place of the second window with the inlet aperture to the reflector defining the actual window. The preferred arrangement is however as described using a true second window and only one reflector.

By measuring the absorption or transmission with the windows present in the light beam and then with selective windows moved out of the light beam it is possible to completely eliminate the influence of the windows on the measurement signal by forming suitable sum and difference values from the signals.

The invention thus starts from the recognition that contamination of the optical boundary surfaces takes place continuously and more or less slowly i.e. that periodic, statistically rapid changes of contamination do not occur. The invention also assumes that the absorption or transmission conditions over the measurement path have not changed during a measurement cycle i.e. that the measurement conditions do not change during the a set of measurements with the windows in the light beam and with certain windows removed from the light beam. If certain changes in the absorption conditions over the measurement path occur during one measurement cycle it is possible to substantially eliminate the resulting error by carrying out several measurement cycles one after the other and by subsequently forming a mean value.

The measures taken in accordance with the invention also take account of spatially irregular contamination on the optical boundary surfaces. It is of particular importance, when using first and second windows, that the second window is completely protected against contamination by the first window for most of the time.

The invention thus provides a method of correctly determining a statistically fluctuating measurement signal even when the level of contamination changes. The invention is particularly advantageous when other protective measures, such as air scavenging of the optical surfaces which are subjected to contamination, fail either wholly or partially.

It is basically possible, when using an arrangement with a light deflector, to arrange the said at least one window only at the light deflector end of the measurement path. In this case the light transmitter/receiver unit must continue to operate with the known zero-point reflector.

The invention however makes it possible to do away with the zero-point reflector which can be swung into the light beam by arranging, in accordance with a third embodiment, for the light transmitter/receiver unit to be accommodated in a housing which is sealingly closed by a window which can be withdrawn from the light beam. A second window which can be moved out of the light beam and, if necessary, replaced by a similar window which is normally protected against external influences is also preferably provided in the housing. In this arrangement, as previously mentioned and in analogy with the arrangement at the light deflector side, the second window is preferably arranged closely behind the first window to define a narrow chamber which is sealingly separated from the interior of the housing by the second window.

In accordance with the invention the arrangement is preferably so contrived that with two windows at each end of the measurement path one is always sealingly arranged at the entrance to the associated housing when the other is removed from the light beam or beam path. It is however possible for two windows, one at each of the two ends of the measurement path, to be simultaneously moved out of the light beam. In the normal case both windows are however located in the light beam in the position in which they seal the housing so that the interior of each of the housings is sealed against the external environment by a lock-like arrangement. For this reason the innermost window remains practically uncontaminated even over long periods of operation. In a simplified embodiment it is sufficient if at least the frontmost window facing the measurement path seals the interior of the associated housing relative to the external environment, that is when the window is positioned in the light beam. The partitioning chambers between the two windows should however be kept as small as possible.

In an autocollimation arrangement the two windows arranged one behind each other need only be provided, as previously mentioned, at the reflector end of the apparatus if a zero-point reflector is used at the light transmitter/receiver end. It is however also basically possible to provide the two removable windows only at the light transmitter/receiver end of the arrangement provided contamination which would significantly impair the measurement result need not be feared at the reflector end of the arrangement, or providing such contamination could be assessed or avoided by other means.

In principle the arrangement can also be such that only the first window is pivoted into the light beam during measurement operation with the second window being pivoted into the light beam only immediately prior to pivoting the first window out of the light beam.

At the light transmitter/receiver end of the apparatus the second window can also take the form of the objective lens associated with the light transmitter/receiver with this lens being replaced during the contamination measurement by an objective which is normally protected against contamination.

In the preferred arrangement the second window is however a separate component and not the objective.

It can also be arranged that only the outer windows facing the measurement path are removed during the contamination measurement whereas the inner windows are manually interchanged or cleaned at widely spaced intervals. In a preferred practical embodiment of the invention the windows which can be moved out of the light beam preferably each comprise a pivotable window mounted to pivot in its plane and arranged to seal against an annular sealing surface of the associated housing when positioned in the light beam.

In one particularly preferred embodiment with first and second windows provided in respect of each of the housings at the two ends of the measurement path a first signal is derived with all the windows positioned in the light beam, a second signal is derived with one of the first and second windows associated with each of the housings moved out of the light beam and a third signal is derived with the other of the first and second windows associated with each of the housings moved out of the light beam. These three measurements are then sufficient to calculate the absorption or transmission along the measurement path independently of the prevailing level of contamination. This arrangement is particularly preferred because the measurement cycle is particularly rapid without in any way impairing the accuracy of the measurement.

In a second preferred arrangement with first and second windows provided in respect of each of the housings at the two ends of the measurement path a first signal is derived with all the windows positioned in the light beam, second and third signals are derived with respective ones of the first and second windows associated with one of the housings moved out of the light beam and fourth and fifth signals are derived with respective ones of the first and second windows associated with the other of the housings moved of the light beam. With this arrangement five measurements are necessary to determine the transmission or absorption along the measurement path independently of the the prevailing level of contamination.

It is particularly advantageous if the first and second windows are automatically moved into and out of the light beam preferably by respective automatically controlled motors.

Figure 2:
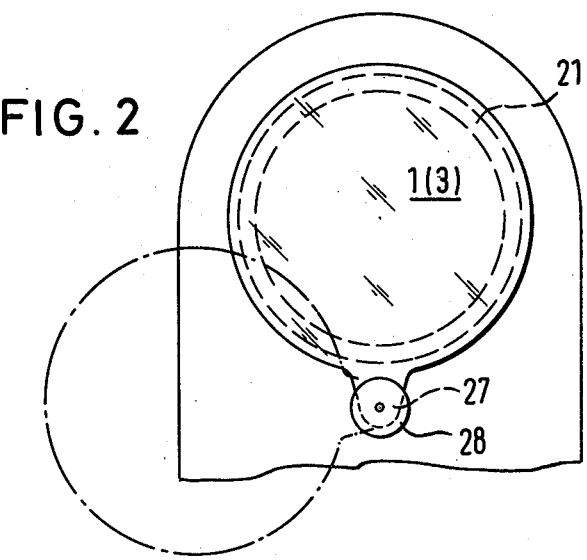

The invention will now be described, by way of example only, with reference to a specific embodiment as shown in the accompanying drawings in which:

FIG. 1 shows a schematic side view of an optical apparatus for measuring optical transmission or absorption in a smoke stack and, FIG. 2 a schematic view on the line 2—2 of FIG. 1 but to a larger scale.

As seen in FIGS. 1 and 2, a light transmitter 17 and a light receiver 18 are accommodated in a common housing 19. The light transmitter 17 comprises a light source 23, an objective 26 and also condenser and slot arrangements which are not shown but are however well known in the art. The light source 23 and the condenser and slot arrangements produce a divergent light beam 24 which passes through a beam divider 25 and falls on an objective 26. The objective 26 forms a parallel light beam 13 which is directed along a measurement path 22 through exhaust gases escaping through a smoke stack onto a retro-reflector 11 arranged at the opposite end of the measurement path 22. The retro-reflector 11 reflects the light beam 13 back on itself so that it once again passes along the measurement path 22 back to the light transmitter/receiver unit where it is concentrated via the objective 26 and the beam divider 25 onto a photoelectric converter 14. The objective 26, the beam divider 25 and the photoelectric converter 14 together form the light receiver part 18 which can if necessary also include further optical elements which are not however shown in detail. The light transmitter 17 is formed by the light source 23, by further optical elements which are not illustrated, by the beam divider 25 and the objective 26. The light transmitter 17 and the light receiver 18 are accommodated, as previously mentioned, in a common housing 19 which is sealed on all sides. The retro-reflector 11 is likewise accommodated in a sealed housing 12.

In accordance with the invention there is provided at the light entry/outlet side of each of the housings 12 19 a respective pair of pivotal windows 1,2 and 3,4 with the windows of each pair of windows being separated from each other by respective narrow partitioning chambers 16 and 20. In the state shown in FIG. 1 and in full lines in FIG. 2 the windows 1,2,3 and 4 are pivoted into a position in the light beam 13 and contact respective annular sealing surfaces or ring seals 21 which cooperate with the windows 1, 2, 3 and 4 to seal the interiors of the housings 12, 19 and the partitioning chambers relative to the outside environment to prevent the entry of contamination. Each of the windows 1,2,3 and 4, which are preferably round in shape in correspondence with the cross-section of the beam path, is arranged via a side disposed flange 27 on the shaft of a respective positioning motor 28. The motor shafts extend parallel to the optical axis and the optical axis extends perpendicular to the planes of the windows 1, 2, 3 and 4. As illustrated in chain dotted lines in FIG. 2, the windows can be pivoted sideways out of the light beam 13 by actuation of the positioning motors 28.

The positioning motors are connected via control lines 29 indicated in broken lines in FIG. 1 with the programming part P of an electronic evaluation circuit 15 which pivots the windows 1, 2, 3 and 4, in a cycle which can be preprogrammed, temporally one after the other into and out of the light beam 13. At any one time at least one of each of the two pairs of windows 1, 2, and 3, 4 is however arranged in the light beam 13 in sealing contact with the associated annular sealing surface 21.

The programme part P also operates a change-over switch 30 which is located in the processing circuit and which allows the electrical signals received from the photoelectric converter 14 to be stored in a memory circuit 31 in dependence on the position of the windows 1 to 4. A computing stage 32 which is connected to the memory circuit 31 calculates, by way of example, the absorption in the absence of windows 1 to 4 from the various measurement signals, $M_I$, $M_{II}$ and $M_{III}$.

The programming unit P can for example first of all specify that the measurement signal $M_I$ should be determined and stored in the memory 31 with all the windows 1 to 4 pivoted into position along the beam 13. The programming unit can then specify that the two windows 2, 4 should be pivoted out of the light beam and the second measurement signal $M_{II}$ determined and stored in the memory 31. Finally the programming unit P can specify that the windows 2 and 4 should be once again pivoted into the light beam and the windows 1 and 3 pivoted out of the light beam. The third measurement signal $M_{III}$ is then determined and stored in the memory. The three measurement signals thus take the following form:

$$M_I = E + E_1 + E_2 + E_3 + E_4 \quad (1)$$

$$M_{II} = E + E_1 + E_3 \quad (2)$$

$$M_{III} = E + E_2 + E_4 \quad (3)$$

where $E$, $E_1$, $E_2$, $E_3$, $E_4$ are the extinctions of the measurement path 22 and the windows 1 to 4 respectively. It will be understood that Extinction = Log$_{10}$ Transmission (sometimes referred to as Transmittance). Transmission is the ratio of the incident light intensity to the transmitted light intensity.

The sum of the measurement signals $M_{II}$ and $M_{III}$ is thus:

$$M_{II} + M_{III} = 2E + E_1 + E_2 + E_3 + E_4 \quad (4)$$

If the first measurement signal $M_I$ is now subtracted from the summed signal M+M in the computing stage 32, then this results in the extinction which would be present in the absence of all the windows 1 to 4:

$$E = M_{II} + M_{III} - M_I \quad (5)$$

It suffices however, if only one of the windows 1 to 4 is pivoted out of the measurement path during each phase of the measurement cycle. In this case the evaluation circuit 15 has to carry out the following calculation:

$$M_I = E + E_1 + E_2 + E_3 + E_4 \quad (6)$$

$$M_{II} = E + E_1 + E_2 + E_3 \quad (7)$$

$$M_{III} = E + E_1 + E_2 + E_4 \quad (8)$$

$$M_{IV} = E + E_1 + E_3 + E_4 \quad (9)$$

$$M_V = E + E_2 + E_3 + E_4 \quad (10)$$

The following calculation must then be carried out in the computing circuit 32 to derive the extinction signal:

$$E = M_{II} + M_{III} + M_{IV} + M_V - 3M_I \quad (11)$$

It is particularly significant that the above described measurement cycles can be carried out separately for each spectral range that is of interest. This is particularly significant, by way of example, for filter wheel measuring apparatus of the type shown from German Auslegeschrift No. 25 21 934.

The various measurement cycles can now be repeated in pre-determined manner until the required level of accuracy is achieved. The individual components, sums and differences are respectively stored in a digital memory and processed in a micro-processor. The method of the invention thus allows an accurate measurement of the extinction E to be carried out up to very high levels of contamination. It is particularly significant that the method of the invention does not at any time require the absorption value of the windows that are used to be determined when the measurement path 22 is free of smoke.

Scavenging air nozzles 33 can also be arranged on the housings 12,19 outside of the outermost windows 1 and 3.

An internal reference reflector (not shown) can be temporarily introduced between the divider 25 and the objective 26 outside of the measurement cycles in order to determine aging of the light source etc.

Apparatus of the invention operates entirely reliably until the total contamination of all the windows 1 to 4 has reached a value corresponding to an absorption of 1. This corresponds to a transmission equal to 0.1.

The arrangement can be used in corresponding manner using more than two windows, or other optical means. Furthermore, the described measurement principle is not restricted to measurement paths including a retro-reflector. The principle can also be used if the light transmitter 17 is arranged at one end of the measurement path 22 and the light receiver 18 is arranged at the other end of the measurement path 22.

If the contamination measured for the inner windows or discs 2,4 exceeds a predetermined value an alarm can be given to draw attention to the fact that the objective 26 or the reflector 11 require cleaning.

The underlying thought is the fact that the windows 4 and 2 will always be contaminated (dirtied) significantly quicker than the respectively associated objective 26 and reflector 11.

Apart from rapid fluctuations of the absorption along the measurement path 22 it is also possible for a systematic rise or fall of the absorption to occur. If the change of absorption which is occurs can be ignored within one measurement cycle, it is advantageous to eliminate the errors that can occur, in accordance with the following computing scheme:

$$E = M_I - \Delta E_1 - \Delta E_2 - \Delta E_3 - \Delta E_4 \quad (12)$$

The values $\Delta E_1$, $\Delta E_2$, $\Delta E_3$, $\Delta E_4$ and the general value $\Delta E_n$ can be found in the following relationship:

$$\Delta E_n = 0.5 E_e - E_a + 0.5 E_n \quad (13)$$

In this equation:

$E_e$ = the measured total extinction immediately before the window in question is pivoted out of the light beam;

$E_a$ = the measured total extinction with the window in question pivoted out of the light beam;

$E_n$ = the measured total extinction with the window in question pivoted back into the light beam.

It shall be appreciated by those skilled in the art that many modifications can be made without departing from the scope of the present teaching as set forth in the appended claims.

It is for example contemplated, in the simplest possible case that, in an autocollimation arrangement, only one pivotable window is provided with this pivotable window being associated with the housing for the retro-reflector. The manner in which the measurement signals must be manipulted for any particular arrangement to yield the absorption or transmission along the measurement path independently of the prevailing level of contamination will be readily apparent to those skilled in the art on considering the origin of the equations set forth in the body of this specification.

I claim:

1. Optical apparatus for measuring absorption in a medium, the apparatus comprising a light transmitter for transmitting a light beam along a measurement path through said medium, a light receiver for receiving said light beam from said light transmitter after it has passed along said measurement path to form signals representative of the absorption between the light transmitter and the light receiver along the measurement path, housing means for accommodating said light transmitter and said light receiver, window means for sealingly closing said housing means, means for periodically moving said window means relative to said housing means into and out of said light beam and a processing circuit for computing the absorption of said light beam in said medium from respective signals obtained with said window means in and out of said light beam.

2. Optical apparatus for measuring transmission or absorption along a measurement path, the apparatus comprising a light transmitter for transmitting a light beam along the measurement path, a light receiver for receiving said light beam from said light transmitter after it has passed along said measurement path, with said light receiver forming signals representative of the transmission or absorption along the measurement path and wherein at least one of said light transmitter, said light receiver and said light deflector is accommodated in a housing which is sealingly closed by at least one window adapted to be moved into and out of said light beam.

3. Optical apparatus according to claim 2 and wherein said light receiver is positioned to receive light directly from said light transmitter and both said light transmitter and light receiver are arranged in respective housing each of which is provided with a said at least one window.

In a second preferred arrangement with first and second windows provided in respect of each of the housings at the two ends of the measurement path a first signal is derived with all the windows positioned in the light beam, second and third signals are derived with respective ones of the first and second windows associated with one of the housings moved out of the light beam and fourth and fifth signals are derived with respective ones of the first and second windows associated with the other of the housings moved of the light beam. With this arrangement five measurements are necessary to determine the transmission or absorption along the measurement path independently of the the prevailing level of contamination.

It is particularly advantageous if the first and second windows are automatically moved into and out of the light beam preferably by respective automatically controlled motors.

The invention will now be described, by way of example only, with reference to a specific embodiment as shown in the accompanying drawings in which:

FIG. 1 shows a schematic side view of an optical apparatus for measuring optical transmission or absorption in a smoke stack and, FIG. 2 a schematic view on the line 2—2 of FIG. 1 but to a larger scale.

As seen in FIGS. 1 and 2, a light transmitter 17 and a light receiver 18 are accommodated in a common housing 19. The light transmitter 17 comprises a light source 23, an objective 26 and also condenser and slot arrangements which are not shown but are however well known in the art. The light source 23 and the condenser and slot arrangements produce a divergent light beam 24 which passes through a beam divider 25 and falls on an objective 26. The objective 26 forms a parallel light beam 13 which is directed along a measurement path 22 through exhaust gases escaping through a smoke stack onto a retro-reflector 11 arranged at the opposite end of the measurement path 22. The retro-reflector 11 reflects the light beam 13 back on itself so that it once again passes along the measurement path 22 back to the light transmitter/receiver unit where it is concentrated via the objective 26 and the beam divider 25 onto a photoelectric converter 14. The objective 26, the beam divider 25 and the photoelectric converter 14 together form the light receiver part 18 which can if necessary also include further optical elements which are not however shown in detail. The light transmitter 17 is formed by the light source 23, by further optical elements which are not illustrated, by the beam divider 25 and the objective 26. The light transmitter 17 and the light receiver 18 are accommodated, as previously mentioned, in a common housing 19 which is sealed on all sides. The retro-reflector 11 is likewise accommodated in a sealed housing 12.

In accordance with the invention there is provided at the light entry/outlet side of each of the housings 12 19 a respective pair of pivotal windows 1,2 and 3,4 with the windows of each pair of windows being separated from each other by respective narrow partitioning chambers 16 and 20. In the state shown in FIG. 1 and in full lines in FIG. 2 the windows 1,2,3 and 4 are pivoted into a position in the light beam 13 and contact respective annular sealing surfaces or ring seals 21 which cooperate with the windows 1, 2, 3 and 4 to seal the interiors of the housings 12, 19 and the partitioning chambers relative to the outside environment to prevent the entry of contamination. Each of the windows 1,2,3 and 4, which are preferably round in shape in correspondence with the cross-section of the beam path, is arranged via a side disposed flange 27 on the shaft of a respective positioning motor 28. The motor shafts extend parallel to the optical axis and the optical axis extends perpendicular to the planes of the windows 1, 2, 3 and 4. As illustrated in chain dotted lines in FIG. 2, the windows can be pivoted sideways out of the light beam 13 by actuation of the positioning motors 28.

The positioning motors are connected via control lines 29 indicated in broken lines in FIG. 1 with the programming part P of an electronic evaluation circuit 15 which pivots the windows 1, 2, 3 and 4, in a cycle which can be preprogrammed, temporally one after the other into and out of the light beam 13. At any one time at least one of each of the two pairs of windows 1, 2, and 3, 4 is however arranged in the light beam 13 in sealing contact with the associated annular sealing surface 21.

The programme part P also operates a change-over switch 30 which is located in the processing circuit and which allows the electrical signals received from the photoelectric converter 14 to be stored in a memory circuit 31 in dependence on the position of the windows 1 to 4. A computing stage 32 which is connected to the memory circuit 31 calculates, by way of example, the absorption in the absence of windows 1 to 4 from the various measurement signals, $M_I$, $M_{II}$ and $M_{III}$.

The programming unit P can for example first of all specify that the measurement signal $M_I$ should be determined and stored in the memory 31 with all the windows 1 to 4 pivoted into position along the beam 13. The programming unit can then specify that the two windows 2, 4 should be pivoted out of the light beam and the second measurement signal $M_{II}$ determined and stored in the memory 31. Finally the programming unit P can specify that the windows 2 and 4 should be once again pivoted into the light beam and the windows 1 and 3 pivoted out of the light beam. The third measurement signal $M_{III}$ is then determined and stored in the memory. The three measurement signals thus take the following form:

$$M_I = E + E_1 + E_2 + E_3 + E_4 \tag{1}$$

$$M_{II} = E + E_1 + E_3 \tag{2}$$

$$M_{III} = E + E_2 + E_4 \tag{3}$$

where E, $E_1$, $E_2$, $E_3$, $E_4$ are the extinctions of the measurement path 22 and the windows 1 to 4 respectively. It will be understood that Extinction = $\log_{10}$ Transmission (sometimes referred to as Transmittance). Transmission is the ratio of the incident light intensity to the transmitted light intensity.

The sum of the measurement signals $M_{II}$ and $M_{III}$ is thus:

$$M_{II} + M_{III} = 2E + E_1 + E_2 + E_3 + E_4 \tag{4}$$

If the first measurement signal $M_I$ is now subtracted from the summed signal M+M in the computing stage 32, then this results in the extinction which would be present in the absence of all the windows 1 to 4:

$$E = M_{II} + M_{III} - M_I \tag{5}$$

It suffices however, if only one of the windows 1 to 4 is pivoted out of the measurement path during each phase of the measurement cycle. In this case the evaluation circuit 15 has to carry out the following calculation:

$$M_I = E + E_1 + E_2 + E_3 + E_4 \quad (6)$$

$$M_{II} = E + E_1 + E_2 + E_3 \quad (7)$$

$$M_{III} = E + E_1 + E_2 + E_4 \quad (8)$$

$$M_{IV} = E + E_1 + E_3 + E_4 \quad (9)$$
$$M_V = E + E_2 + E_3 + E_4 \quad (10)$$

The following calculation must then be carried out in the computing circuit 32 to derive the extinction signal:

$$E = M_{II} + M_{III} + M_{IV} + M_V - 3M_I \quad (11)$$

It is particularly significant that the above described measurement cycles can be carried out separately for each spectral range that is of interest. This is particularly significant, by way of example, for filter wheel measuring apparatus of the type shown from German Auslegeschrift No. 25 21 934.

The various measurement cycles can now be repeated in pre-determined manner until the required level of accuracy is achieved. The individual components, sums and differences are respectively stored in a digital memory and processed in a micro-processor. The method of the invention thus allows an accurate measurement of the extinction E to be carried out up to very high levels of contamination. It is particularly significant that the method of the invention does not at any time require the absorption value of the windows that are used to be determined when the measurement path 22 is free of smoke.

Scavenging air nozzles 33 can also be arranged on the housings 12,19 outside of the outermost windows 1 and 3.

An internal reference reflector (not shown) can be temporarily introduced between the divider 25 and the objective 26 outside of the measurement cycles in order to determine aging of the light source etc.

Apparatus of the invention operates entirely reliably until the total contamination of all the windows 1 to 4 has reached a value corresponding to an absorption of 1. This corresponds to a transmission equal to 0.1.

The arrangement can be used in corresponding manner using more than two windows, or other optical means. Furthermore, the described measurement principle is not restricted to measurement paths including a retro-reflector. The principle can also be used if the light transmitter 17 is arranged at one end of the measurement path 22 and the light receiver 18 is arranged at the other end of the measurement path 22.

If the contamination measured for the inner windows or discs 2,4 exceeds a predetermined value an alarm can be given to draw attention to the fact that the objective 26 or the reflector 11 require cleaning.

The underlying thought is the fact that the windows 4 and 2 will always be contaminated (dirtied) significantly quicker than the respectively associated objective 26 and reflector 11.

Apart from rapid fluctuations of the absorption along the measurement path 22 it is also possible for a systematic rise or fall of the absorption to occur. If the change of absorption which is occurs can be ignored within one measurement cycle, it is advantageous to eliminate the errors that can occur, in accordance with the following computing scheme:

$$E = M_I - \Delta E_1 - \Delta E_2 - \Delta E_3 - \Delta E_4 \quad (12)$$

The values $\Delta E_1$, $\Delta E_2$, $\Delta E_3$, $\Delta E_4$ and the general value $\Delta E_n$ can be found in the following relationship:

$$\Delta E_n = 0.5 E_e - E_a + 0.5 E_n \quad (13)$$

In this equation:
 $E_e$ = the measured total extinction immediately before the window in question is pivoted out of the light beam;
 $E_a$ = the measured total extinction with the window in question pivoted out of the light beam;
 $E_n$ = the measured total extinction with the window in question pivoted back into the light beam.

It shall be appreciated by those skilled in the art that many modifications can be made without departing from the scope of the present teaching as set forth in the appended claims.

It is for example contemplated, in the simplest possible case that, in an autocollimation arrangement, only one pivotable window is provided with this pivotable window being associated with the housing for the retro-reflector. The manner in which the measurement signals must be manipulted for any particular arrangement to yield the absorption or transmission along the measurement path independently of the prevailing level of contamination will be readily apparent to those skilled in the art on considering the origin of the equations set forth in the body of this specification.

I claim:
1. Optical apparatus for measuring absorption in a medium, the apparatus comprising a light transmitter for transmitting a light beam along a measurement path through said medium, a light receiver for receiving said light beam from said light transmitter after it has passed along said measurement path to form signals representative of the absorption between the light transmitter and the light receiver along the measurement path, housing means for accommodating said light transmitter and said light receiver, window means for sealingly closing said housing means, means for periodically moving said window means relative to said housing means into and out of said light beam and a processing circuit for computing the absorption of said light beam in said medium from respective signals obtained with said window means in and out of said light beam.

2. Optical apparatus for measuring transmission or absorption along a measurement path, the apparatus comprising a light transmitter for transmitting a light beam along the measurement path, a light receiver for receiving said light beam from said light transmitter after it has passed along said measurement path, with said light receiver forming signals representative of the transmission or absorption along the measurement path and wherein at least one of said light transmitter, said light receiver and said light deflector is accommodated in a housing which is sealingly closed by at least one window adapted to be moved into and out of said light beam.

3. Optical apparatus according to claim 2 and wherein said light receiver is positioned to receive light directly from said light transmitter and both said light transmitter and light receiver are arranged in respective housing each of which is provided with a said at least one window.

4. Optical apparatus according to claim 2 and wherein said light receiver and said light transmitter are arranged in a common housing at one end of said measuring path and said light deflector is arranged in a further housing at the other end of said measuring path and wherein both said common housing and said further housing are provided with a said at least one window.

5. Optical apparatus in accordance with either of claims 3 or 4 and wherein each said housing is provided with a respective second window which can be moved out of said light beam.

6. Optical apparatus in accordance with claim 5 and wherein each said second window can be replaced by an equivalent window which is usually shielded from external influences.

7. Optical apparatus in accordance with claim 5 and wherein each said second window is arranged closely behind the associated first said window thereby defining a narrow chamber therebetween.

8. Optical apparatus in accordance with claim 7 and wherein each said second window acts to sealingly separate said narrow chamber from the interior of the associated housing.

9. Optical apparatus in accordance with claim 5 and wherein each said second window comprises a pivotable window mounted to pivot in its plane and arranged to seal against a respective annular sealing surface of the associated housing when positioned in said light beam.

10. Optical apparatus in accordance with claim 5 and wherein said light receiver comprises photoelectric converter means for generating said signals and wherein said photelectric converter means is connected to an electronic processing circuit for processing said signals to calculate the transmission or absorption along said measurement path.

11. Optical apparatus in accordance with claim 10 and wherein said electronic processing circuit operates to calculate the transmission or absorption along said measurement path without any said windows from a first signal ($M_I$) derived with all said windows positioned in said light beam; from a second signal ($M_{II}$) derived with one of the first second windows associated with each of the housings moved out of said light beam and from a third signal ($M_{III}$) derived with the other of the first and second windows associated with each of the housings moved out of said light beam.

12. The combination of optical apparatus in accordance with claim 11 with a microprocessor for controlling the movements of said first and second windows.

13. The combination of claim 12 and wherein the miroprocessor also forms processing circuitry for processing said first, second and third signals.

14. Optical apparatus in accordance with claim 10 wherein said electronic processing circuit operates to calculate the transmission or absorption along said measurement path without any said windows from first signals ($M_I$) derived with all said windows positioned in said light beam, from second signals ($M_{II}$ and $M_{III}$) derived with respective ones of the first and second windows associated with one of the housings moved out of the light beam and from fourth and fifth signals ($M_{IV}$ and $M_V$) derived with the first and second windows associated with the other of the housings moved out of the light beam.

15. The combination of optical apparatus in accordance with claim 14 with a microprocessor for controlling the movements of said first and second windows.

16. The combination of claim 15 and wherein the microprocessor also forms processing circuitry for processing said first, second, third, fourth and fifth signals.

17. Optical apparatus in accordance with claim 5 and wherein further windows are associated with each said housing and can be positioned or moved out of said light beam.

18. Optical apparatus in accordance with either of claims 3 or 4 and wherein automatic means is provided for cyclically moving each said at least one window into and out of said light beam.

19. Optical apparatus in accordance with claim 18 and wherein said automatic means comprises an automatically controlled motor.

20. Optical apparatus in accordance with any one of claims 2, 3 or 4 and wherein the or each said at least one window comprises a pivotable window mounted to pivot in its plane and arranged to seal against an annular sealing surface of the associated housing when positioned in said light beam.

21. Optical apparatus in accordance with claim 4 and wherein each said housing is provided with a respective second window which can be moved out of said light beam and wherein said second windows are defined by a common objective lens associated with said light transmitter and said light receiver and by a retroreflector forming with said light deflector respectively.

22. A method of measuring transmission or absorption along a measurement path using the apparatus of claim 21, said method comprising the step of forming a summed value equivalent to the second signal plus the third signal less the first signal.

23. Optical apparatus in accordance with claim 4 and wherein said light deflector comprises a retroreflector.

24. A method of measuring transmission or absorption along a measured path using the apparatus of claim 23 said method comprising the steps of forming a summed value equivalent to the sum of the second signal, the third signal, the fourth signal and the fifth signal less three times the first signal.

25. Optical apparatus in accordance with claim 2 and wherein further automatic means is provided for cyclically moving each said second window into and out of said light beam.

26. Optical apparatus in accordance with claim 25 and wherein said further automatic means comprises an automatically controlled motor.

27. Optical apparatus in accordance with claim 2 and wherein said at least one window can be moved intermittently into and out of said light beam.

* * * * *